United States Patent
Bartlett (10) Patent No.: US 11,185,446 B2
(45) Date of Patent: Nov. 30, 2021

(54) METHOD AND APPARATUS FOR CORRECTING AURICULAR DEFORMITIES

(71) Applicant: The Children's Hospital of Philadelphia, Philadelphia, PA (US)

(72) Inventor: Scott P Bartlett, Philadelphia, PA (US)

(73) Assignee: THE CHILDREN'S HOSPITAL OF PHILADELPHIA, Philadelphia, PA (US)

(*) Notice: Subject to any disclaimer, the term of this patent is extended or adjusted under 35 U.S.C. 154(b) by 0 days.

(21) Appl. No.: 14/758,877

(22) PCT Filed: Jan. 2, 2014

(86) PCT No.: PCT/US2014/010102
§ 371 (c)(1),
(2) Date: Jul. 1, 2015

(87) PCT Pub. No.: WO2014/107532
PCT Pub. Date: Jul. 10, 2014

(65) Prior Publication Data
US 2015/0335491 A1    Nov. 26, 2015

Related U.S. Application Data

(60) Provisional application No. 61/748,240, filed on Jan. 2, 2013.

(51) Int. Cl.
*A61F 11/14*    (2006.01)
*A61F 11/08*    (2006.01)
(Continued)

(52) U.S. Cl.
CPC .......... *A61F 11/14* (2013.01); *A61F 5/01* (2013.01); *A61F 11/004* (2013.01); *A61F 11/08* (2013.01)

(58) Field of Classification Search
CPC ...... A61F 11/00; A61F 11/004; A61F 11/008; A61F 11/04; A61F 11/06; A61F 11/08;
(Continued)

(56) References Cited

U.S. PATENT DOCUMENTS

| 1,062,654 A | 5/1913 | Lowman |
| 1,338,090 A | 4/1920 | Parvin |

(Continued)

FOREIGN PATENT DOCUMENTS

| CA | 1078690 | 6/1980 |
| CH | 208142 A | 12/1969 |

(Continued)

OTHER PUBLICATIONS

Extended European Search Report dated Jul. 18, 2016 for European Application No. 14735382.5, 7 pages.
(Continued)

*Primary Examiner* — Rachael E Bredefeld
*Assistant Examiner* — Rachel A Berezik (57) ABSTRACT

An auricular support system can include a substrate and a mold material. The substrate can include a substrate body having a first end and an opposed second end. At least a portion of the first end can be configured to carry an adhesive suitable to attach to a dermal surface. The second end defines at least one void. The mold material can be configured to be applied to both an auricular structure and the second end of the substrate body such that the mold material becomes disposed in the void and molds about the auricular structure. The mold material can be configured to cure after the mold material is applied to the auricular structure and the substrate body so as to support the auricular structure relative to the substrate. The auricular support system can further include an auxiliary support structure configured to attach to the auricular structure.

16 Claims, 4 Drawing Sheets

(51) Int. Cl.
*A61F 11/00* (2006.01)
*A61F 5/01* (2006.01)

(58) Field of Classification Search
CPC .. A61F 11/10; A61F 11/14; A61F 5/01; A61F 5/0102; A61F 2/18; A61F 2002/183; A61F 13/0213; A61F 11/12; A61F 2007/0005; A45D 44/12
See application file for complete search history.

(56) References Cited

U.S. PATENT DOCUMENTS

| | | | |
|---|---|---|---|
| 2,339,572 A | | 1/1944 | Jurovaty |
| 3,674,181 A | * | 7/1972 | Marks ............... A61M 3/00 222/179.5 |
| 3,841,325 A | | 10/1974 | Pickard |
| 3,925,277 A | * | 12/1975 | Lampe ............... C08L 83/04 128/864 |
| 4,015,602 A | * | 4/1977 | Nelson ............... A61F 11/00 222/561 |
| 4,134,153 A | | 1/1979 | Voorhees |
| 4,187,838 A | | 2/1980 | Dubrowski |
| 4,616,643 A | | 10/1986 | Jung |
| 4,959,265 A | | 9/1990 | Wood et al. |
| 5,522,896 A | * | 6/1996 | Prescott ............ A61B 17/0057 623/23.56 |
| 5,737,436 A | | 4/1998 | Boyden |
| 5,749,099 A | | 5/1998 | Voorhees |
| 6,517,557 B1 | | 2/2003 | Sorribes |
| 7,028,343 B1 | | 4/2006 | Watson |
| 7,093,600 B2 | | 8/2006 | Sorribes |
| 7,850,702 B2 | | 12/2010 | Sorribes |
| 8,136,530 B2 | | 3/2012 | Byrd et al. |
| 2003/0167556 A1 | | 9/2003 | Kelley |
| 2005/0224082 A1 | * | 10/2005 | Johnson ............... A61F 11/08 128/864 |
| 2008/0264715 A1 | * | 10/2008 | Leong ............... A61F 11/08 181/135 |
| 2009/0030358 A1 | * | 1/2009 | Byrd ............... A61F 5/01 602/17 |
| 2010/0059078 A1 | | 3/2010 | Winters |
| 2010/0204793 A1 | * | 8/2010 | Byrd ............... A61F 5/0102 623/10 |
| 2011/0264236 A1 | | 10/2011 | Bassett |
| 2012/0017359 A1 | | 1/2012 | Parris et al. |
| 2012/0124719 A1 | * | 5/2012 | Michlitsch ............ A41D 13/05 2/423 |
| 2012/0179078 A1 | * | 7/2012 | Koehler ............ A61F 11/004 602/2 |
| 2013/0068238 A1 | * | 3/2013 | Parris ............... A45D 44/12 128/866 |

FOREIGN PATENT DOCUMENTS

| | | |
|---|---|---|
| CN | 202478412 | 10/2012 |
| DE | 102006007032 | 8/2007 |
| DE | 202007016893 U1 | 2/2008 |
| DK | 174399 B1 | 2/2003 |
| EP | 0047270 B1 | 10/1984 |
| EP | 2100574 | 9/2009 |
| GB | 14949 | 12/1911 |
| GB | 10220 | 2/1912 |
| GB | 1415209 A | 11/1975 |
| GB | 2304579 A | 3/1997 |
| JP | 1014971 A | 1/1998 |
| JP | 2010534112 A | 11/2010 |
| JP | 5496092 B2 | 5/2014 |
| WO | 8102515 A1 | 9/1981 |
| WO | 9409731 | 5/1994 |
| WO | 9831314 A1 | 7/1998 |
| WO | 20090014908 | 1/2009 |
| WO | 2010107364 A1 | 9/2010 |

OTHER PUBLICATIONS

Byrd, H.S. et al., "Ear Molding in Newborn Infants with Auricular Deformities," Plastic and Reconstructive Surgery, vol. 126, No. 4, Oct. 2010, pp. 1191-1200.
International Preliminary Report on Patentability for International Application No. PCT/US2014/010102 dated Jul. 7, 2015.
International Search Report for International Application No. PCT/US2014/010102 dated Mar. 21, 2014.
Stanford University School of Medicine, "Ear Device Corrects Newborn Ear Deformities Without Surgery," Jan. 24, 2011 [retrieved on Mar. 6, 2014], retrieved from the internet: <http://med.stanford.edu/ism/2011/january/ear-0124.html>.
Written Opinion of the International Searching Authority for International Application No. PCT/US2014/010102 dated Mar. 21, 2014.
Australian Examination Report for Australian Application No. 2014204042, dated Jun. 19, 2017, 3 pages.
Notice of Reasons for Rejection for Japanese Application No. 2015-551758, dated Oct. 18, 2017, including English language translation, 6 pages.
Sorribes, M., et al., "Nonsurgical Treatment of Prominent Ears with the Auri Method," Dec. 2002, pp. 1369-1376, vol. 128(12), Archives of Otolaryngology Head & Neck Surgery.
Notice of Reasons for Rejection for Japanese Application No. 2015-551758, dated Jul. 3, 2018, with translation, 4 pages.
Communication of a Notice of Opposition and Notice of Opposition for European Application No. 14735382.5, dated Dec. 4, 2018, 18 pages.
Communication of Notices of Opposition (R.79(1) EPC) for European Application No. 14735382.5, dated Dec. 10, 2018, 1 page.
Response to Notice of Opposition for European Application No. 14735382.5, dated Apr. 23, 2019 with Feature Analysis of the claims as granted and Claim set of first and second auxiliary requests, 34 pages.
Reinisch et al., "Ear Reconstruction Using a Porous Polyethylene Framework and Temporoparietal Fascia Flap", Facial Plastic Surgery, vol. 25, No. 3, 2009, pp. 181-189.
Roberts, "Facial Reconstruction By Prosthetic Means", British Journal of Oral Surgery, 1966, pp. 157-182.
Heman-Ackah et al., "Use of Silicone Hearing Aid Mold Material In Laryngotracheal Reconstruction", US National Library of Medicine National Institutes of Health, 2005, 6 pages.
Macdonald et al., "Case Presentation: A Novel Way of Treating Acute Cauliflower Ear in a Professional Rugby Player", British Journal Sports Med., 2005, vol. 23, 2 pages.
"Auricular Hematoma Drainage", available from https://www.thehealthscience.com/topics/auricular-hematoma-drainage, cited Nov. 24, 2018, 9 pages.
Tarhiri, "Medpor Ear Reconstruction and Instructions for Silicone Mold", 2018, available from https://www.microtiarepair.com/medpor-ear-reconstruction/ and https://www.microtiarepair.com/instructions-for-silicon-mold, 10 pages.
Amended claims—Eighth Auxiliary Request in Opposition Proceeding for European Patent No. 2 941 224, dated Jul. 30, 2020.
Amended claims—Seventh Auxiliary Request in Opposition Proceeding for European Patent No. 2 941 224, dated Jul. 30, 2020.
Response to Addendum to Preliminary Opinion in Opposition Proceeding for European Patent No. 2 941 224, dated Jul. 30, 2020.
Summons to Attend Oral Proceedings in Opposition Proceeding for European Patent No. 2 941 224, dated Jun. 5, 2020.
Summons to Attend Oral Proceedings Pursuant to Rule 115(1) for European Application No. 14 735 382.5, dated Jul. 15, 2019, 12 pages.
Hall, "Kit Cures Stick-out-ears without need for surgery", The Telegraph, 2005, 3 pages.
Dancy et al., "Acrylic Ear Molding", Letters and Viewpoints, vol. 115, No. 7, pp. 2142-2175.
Sprekelsen et al., "Die Konservative Korrektur Angeborener Formanomalien der Ohrmuschel", Laryngo-Rhine-Otol, 1990, vol. 69, pp. 581-585.

(56) References Cited

OTHER PUBLICATIONS

Brown et al., "Correction of Congenital Auricular Deformities by Splinting in the Neonatal Period", Pediatrics, 1986, vol. 78, No. 3, pp. 406-411.
Byrd et al., "Ear Molding in Newborn Infants with Auricular Deformities", Plastic and Reconstructive Surgery, 2010, pp. 1191-1199.
Chang et al., A Simplified Nonsurgical Method for the Correction of Neonatal Deformational Auricular Anomalies, Clinical Pediatrics, 2017, vol. 56, No. 2, pp. 132-139.
Earbuddies Ear Shape Corrector for Babies, Infants, Toddlers,—Premium Kit No. 1921145285, downloaded fro https://www.worthpoint.com/worthopedia/earbuddies-ear-shape-corrector-babies-19211452785, 2019, 5 pages.
EarBuddies Sales to Hospitals, Clinics & Health Professionals, downloaded from https://www.earbuddies.co.uk/pages/healthcare-professionals, 2019, 3 pages.
Economides et al., "Discussion: A Morphometric Study of the Newborn Ear and an Analysis of Factors Related to Congenital Auricular Deformities", Discussion, vol. 140, No. 1, 2 pages.
Declaration of Meir D. Hershcovitch re: *Talexmedical, LLC v. Beacon Medical Limited and Henry Stephenson Byrd*, 2019, 87 pages.
Gray's Anatomy, Anatomy of the Human Body, "The Organs of the Senses", 1959, p. 1126.
Hirose, "Non Sugfical Correction of Cryptotia Using Simple Apparatus", Transations of the Seventh International Congress of Plastic and Reconstructive Surgery, 1979, 3 pages.
Yotsuyanagi et al., The Use of a Thermoplastic Splint for Treating Cryptotia, Plastic Surgr., vol. 36, No. 9, 1993, pp. 1037-1042.
Kamiishi et al., "Evaluation of a Simple Prosthesis for Correction of Cryptotia", Keisei Geka, Plastic & Reconstructive, 1976, vol. 19, pp. 7-12.
Kurozumi et al., "Non-Surgical Correction of a Cogenital Lop Ear Deformity by Splinting with Reston Foam", British Journal of plastic Surgery, 1982, vol. 35, pp. 181-182.
Linford et al., "Postpartum Splinting of Ear Deformities", BMJ, 2007, vol. 334, pp. 366-368.
Matsuo et al., "Nonsurgical Correction of Congenital Auricular Deformities", Clinics in Plastic Surgery, 1990, vol. 17, No. 2, pp. 383-395.
Muroaka et al., "A Simple Prosthesis For Correction of Cryptotia", Laryngoscope, 1984, vol. 94, 8 pages.
Smith et al., "Nonsurgical Correction of Congenital Ear Abnormalities in the Newborn: Case Series", Pediatric Child Health, 2005, vol. 10, No. 6, pp. 327-331.
Yotsuyanagi et al., "Nonsurgical Correction of Congenital Auricular Deformities in Children Older than Early Neonates" Plastic and Reconstructive Surgery, 1998, pp. 907-914.
Park, "Correction of Cryptotia Using an External Stretching Device", Annals of Plastic Surger, 2002, vol. 48, No. 5, pp. 534-538.
Petition for Inter Partes Review of U.S. Pat. No. 8,852,277 re: *Talexmedical, LLC v. Beacon Medical Limited and Henry Stephenson Byrd*, dated Oct. 9, 2019, 52 pages.
Petition for Inter Partes Review of U.S. Pat. No. 8,167,942 re: *Talexmedical, LLC v. Beacon Medical Limited and Henry Stephenson Byrd*, dated Oct. 9, 2019, 59 pages.
Merlob et al., "Splinting Therapy for Congenital Auricular Deformitis with the Use of Soft Material", Journal of Perinatology, vol. 15, No. 4, pp. 294-296.
Tan et al., "A Splint for Correction of Congenital Ear Deformities", British Journal of Plastic Surgery, 1994, vol. 47, pp. 575-578.
Ullmann et al., "Early Non surgical Correction of Congenital Auricular Deformities", Plastic and Reconstructive Surgery, 2002, vol. 109, No. 3, pp. 907-913.
Weerda, Surgery of the Auricle, Tumors Trauma Defects Abnormalities, 2007, 329 pages.
Yotsuyanagi, "Nonsurgical Correction of Congenital Auricular Deformities in Children Older than Early Neonates" (Follow Up), pp. 190-191.
Zhao et al., "A Morphometric Study of the Newborn Ear and an Analysis of Factors Related to Congenital Auricular Deformities", Plastic and Reconstructive Surgrery, 2017, pp. 147-155.
Canadian Examination Report for Canadian Application No. 2896954, dated Dec. 5, 2019, 6 pages.
Office Action received in Canadian Application No. 2,896,954, dated Aug. 18, 2020, 6 pages.
Response to Office Action filed in Canadian Application No. 2,896,954, filed Dec. 11, 2020, 14 pages.
"Decision Revoking the European Patent" received in European Patent No. 2 941 224, dated Sep. 20, 2021, 42 pages.

* cited by examiner

METHOD AND APPARATUS FOR CORRECTING AURICULAR DEFORMITIES

CROSS-REFERENCE TO RELATED APPLICATIONS

This application is the U.S. National Phase Application of PCT International Application No. PCT/US2014/010102, filed Jan. 2, 2014, which claims the benefit of U.S. Provisional Application No. 61/748,240, filed Jan. 2, 2013, the contents of both applications being incorporated by reference herein as if set forth in their entirety.

BACKGROUND

A significant number of infants are born with some form of auricular deformity. Further, infants born without an auricular deformity can cause damage to the ear in the hours and days after birth, for instance due to contact with a mattress, a car seat, or the like. Examples of auricular deformities in newborn infants include conditions that result from a lack of auricular tissue, an excess of auricular tissue, and incorrectly shaped auricular tissue.

It has been found that increased levels of estrogen present in newborn infants produce advantageous pliable effects in auricular cartilage. As a result, if the ear is placed and held in a desired anatomic position early in life, the ear will be molded into a more natural shape and fixed over a brief period of time. As the infant ages, the levels of estrogen decrease, which causes the cartilage to becomes less malleable and more rigid. The reduced malleability and increased rigidity of the ear cartilage reduces the ability to reposition auricular deformities. For instance, it has been found that success rates of attempts to alter anatomical aspects of the ear after 3 weeks of life can decrease by more than 50% with respect to initiating such attempts before the expiration of 3 weeks of life.

Ear repositioning systems currently exist that include fixation devices designed to address auricular deformities in newborn infants. However, such systems can rely upon double-sided tape to attach to both the skin surface and the fixation devices. However, the adhesion of the tape to the skin surface can become compromised, which causes maintenance of the fixation devices to be labor intensive. In some instances, the fixation devices and tape are administered by guardians of the infant at home, which can result in improper application of the fixation devices. Some conventional systems include an ear well is adhesively attached, for instance via double-sided tape, to the cranial skin surface that surrounds the ear. The ear well thus surrounds the ear and supports auxiliary structure that attaches to various portions of the ear so as to maintain the ear portions in a desired position. However, the ear well does not provide much positional flexibility of the auxiliary structure. Furthermore, the adhesion of the ear well to the outer skin surface can degrade, for instance at the mastoid region due to movement of the mandible during normal anatomical operations. Still other conventional ear positioning systems comprise various splints and other fixation devices created by clinicians on a case-by-case basis.

SUMMARY

In accordance with one embodiment, an auricular support system can include a substrate and a mold material. The substrate can include a substrate body having a first end and an opposed second end. At least a portion of the first end can be configured to carry an adhesive suitable to attach to a dermal surface. The second end defines at least one void. The mold material can be configured to be applied to both an auricular structure and the second end of the substrate body such that the mold material becomes disposed in the void and molds about the auricular structure. The mold material can be configured to cure after the mold material is applied to the auricular structure and the substrate body so as to support the auricular structure relative to the substrate.

DESCRIPTION OF THE DRAWINGS

The foregoing summary, as well as the following detailed description of an example embodiment of the application, will be better understood when read in conjunction with the appended drawings, in which there is shown in the drawings an example embodiment for the purposes of illustration. It should be understood, however, that the application is not limited to the precise arrangements and instrumentalities shown. In the drawings.

DETAILED DESCRIPTION

Figure 1A:
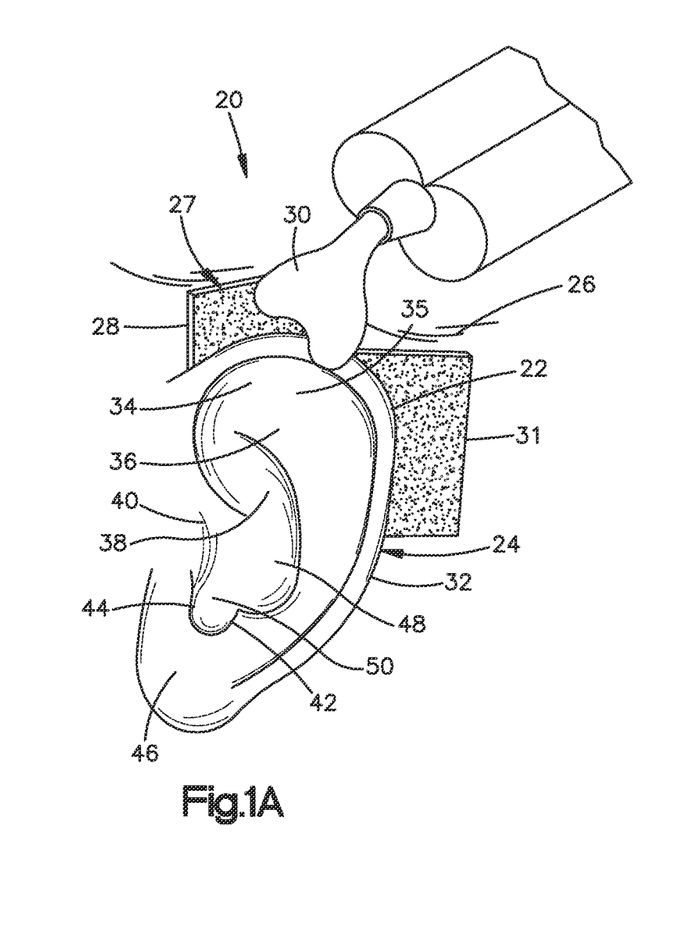
FIG. 1A is a perspective view of an auricular support system including a mold material and a substrate configured to attach to a dermal surface, showing the substrate attached to a dermal surface adjacent an auricle.

Referring to FIG. 1A, an auricular support system 20 is configured to support various auricular structure 22, for instance of an auricle 24, relative to a dermal surface 26 of the cranium that is disposed adjacent the auricle 24, for instance medial with respect to the auricle, such that the auricular structure 22 is maintained at a position that is spaced from the dermal surface 26 at a desired distance. The auricular support system 20 can be further configured to maintain the auricular structure 22 in a desired shape, so as to correct for a deformity in a newborn infant.

Figure 1B:
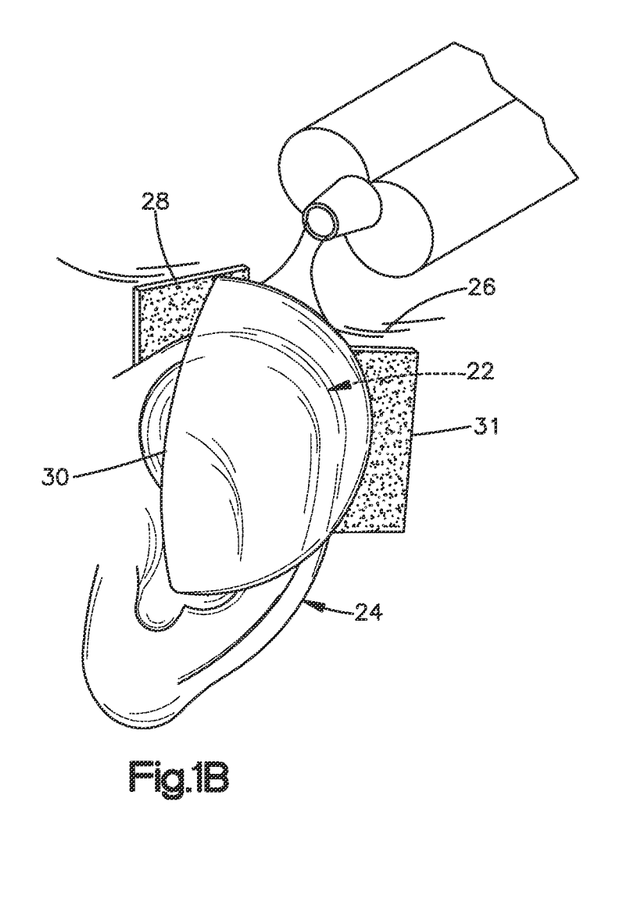
FIG. 1B is a perspective view of the auricular support system, showing the mold applied to the auricle and the substrate.

Referring to FIG. 1A, the auricular support system 20 constructed in accordance with one embodiment can include at least one substrate 27 that is configured to attach to a dermal surface 26 that is disposed adjacent the auricle 24, and a mold material 30, such as a gel, that is configured to be applied in a gelatinous state to the auricle 24 and the at least one substrate 27. The mold material 30 can then be allowed to cure, such that the mold material 30 attaches to both the auricle 24 and the substrate 27, thereby supporting the auricle 24 relative to the substrate 27. For instance, referring also to FIG. 1B, the mold material 30 is configured to mold about an auricular structure of the auricle 24, including at least one or more, up to all of the helical rim 32, the triangular fossa 34, the helical crux 35, the antihelix 36, the concha 38, the tragus 40, the antitragus 42, the external auditory meatus 44, the lobule 46, and can further extend into the conchal cavity 48 and the ear canal 50. Once the mold material has cured about the auricular structure of the auricle 24, mechanical interference between the auricular structure and the cured mold material 30 prevents inadvertent removal of the cured mold material 30 from the auricle 24.

Figure 2A:
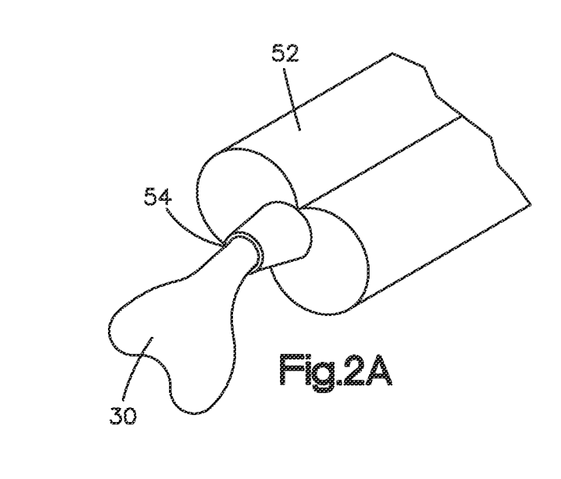
FIG. 2A is a perspective view of a mold material disposed in a dispenser.

As illustrated in FIG. 2A, the mold material 30 can be disposed in a housing 52, which can be configured as dispenser, that defines an outlet opening 54. In accordance with one embodiment, the housing 52 can be configured as a tube. The housing 52 can be flexible, such that during operation an inwardly directed squeezing force causes the housing 52 to deform, thereby inducing a positive internal pressure that forces a quantity of the mold material out the opening 54. It should be appreciated that the housing 52 can be alternatively configured to dispense a quantity of the mold material 30 as desired. The mold material 30 can be provided as any suitable biocompatible mold material that is suitable to be applied to the auricular structure 22 and the substrate 27 in a gelatinous state, and subsequently cured so as to at least partially surround a structure of the auricular structure 22 and the substrate 27, thereby resisting separation with respect to the auricular structure 22 and the substrate 27. It should thus be appreciated that the mold material 30 can define a gel, which can be provided as a polymer. For instance, the gel can be an elastomer, such as silicone. It should be further appreciated that the gel can be a two-part pliable polymer, wherein first and second parts of the polymer mix so as to activate the polymer, such that the polymer can cure a short duration after being dispensed from the housing 52. For instance, in accordance with one embodiment, the mold material can be a polymer sold under the name Memosil, Memosil 2, or Memosil C.D. commercially available from Hareaus Kulzer, having a place of business in Armonk, N.Y.

Figure 2B:
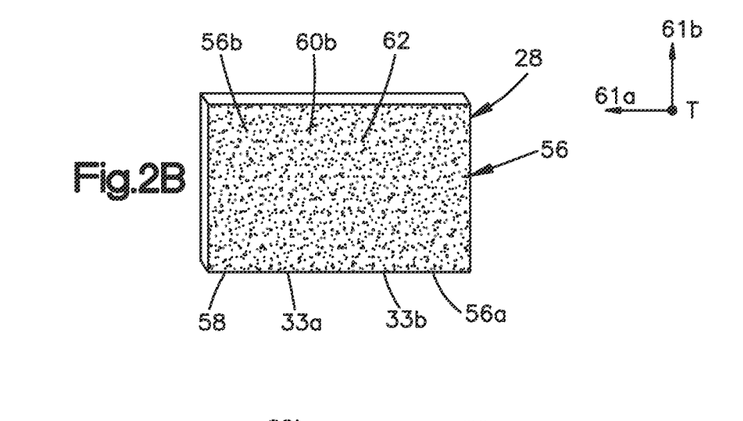
FIG. 2B is a perspective view of a first substrate.

Referring now to FIG. 2B, the at least one substrate 27 can include a substrate 28 that includes a substrate body 56 having a first end 56a is configured to carry an adhesive 58 that is suitable to attach to the dermal surface 26, and a second end 56b opposite the first end 56a. The second end 56b can define at least one void 59 such as a plurality of voids 59 that are configured to receive the mold material 30 that is applied to the substrate 28. Thus, it should be appreciated that the second end 56b of the substrate body 56 can include a matrix that defines the voids 59. For instance, the first end 56a can define a first surface 60a and an opposed second surface 60b that is spaced from the first surface 60a along a transverse direction T. At least a portion of the first surface 60a is configured to carry the adhesive 58. The substrate body 56, such as the second end 56b of the substrate body 56, can further include a at least one finger 62, such as a plurality of fingers 62, that project out from at least a portion of the second surface 60b. Thus, the substrate body 56, for instance at the second end 56b, can define a matrix of fingers 62 that project out from the second surface 60b. The fingers 62 can be configured as hooks, loops, or any suitable constructed alternative projection suitable for at least partially defining the voids 59 that can receive the applied mold material 30 so as to attach the fingers 62, and thus the substrate, to the mold material 30 once the mold material 30 has cured. Thus, it can be said that the matrix of fingers 62 of the substrate body 56 can project from the second surface 60b. In accordance with one embodiment, the at least one substrate 27 is commercially available under the trademark Velcro® from Velcro USA Inc, having a place of business in Manchester, N.H.

Thus, it should be appreciated that the fingers can extend out from the second surface 60b along both the transverse direction T and a direction perpendicular to the transverse direction T, such that the void 59 can be defined between the second surface 60b of the first end 56a and a portion of the second end 56b, which can be defined by the fingers 62, along the transverse direction T. The first end 56a can extend generally along at least a first direction, such that the voids 59 extend between the respective fingers 62 and the second surface 56b. It should thus be appreciated that when the mold material 30 is applied to the auricular structure 22 and the second end 56b of the substrate body 56, the mold material can become disposed in the void 59 and mold about the auricular structure 22. Thus, when the mold material 30 cures after the mold material 30 is applied to the auricular structure 22 and the substrate body 56, the mold material 30 supports the auricular structure 22 relative to the substrate 28. During operation, at least a portion of the first end 56a of the substrate body 56 can be attached to the dermal surface 26, and the auricular structure 22 can be manipulated as desired so as to correct a deformity of the auricular structure 22.

For instance, the auricular structure 22 can be stretched, compressed, bent, straightened, placed further from the dermal surface 26, or placed closer to the dermal surface 26, or can be alternatively manipulated as desired so as to correct the deformity. The mold material 30 can then be applied to the manipulated auricular structure 22 and the substrate 28 and allowed to cure as described above, so as to maintain the manipulated configuration of the auricular structure 22. Once it is desired to remove the auricular support system 20, a free edge of the cured mold material 30 can be gripped and peeled away from, and thus removed from, the auricular structure 22. The substrate 28 can be further removed from the dermal surface 26, thereby removing the mold material 30 from the dermal surface 26. Alternatively or additionally, the mold material 30 can be peeled away from, and thus removed from, the substrate 28, and thus removed from the dermal surface 26, before the substrate 28 is removed from the dermal surface 26.

Figure 2C:
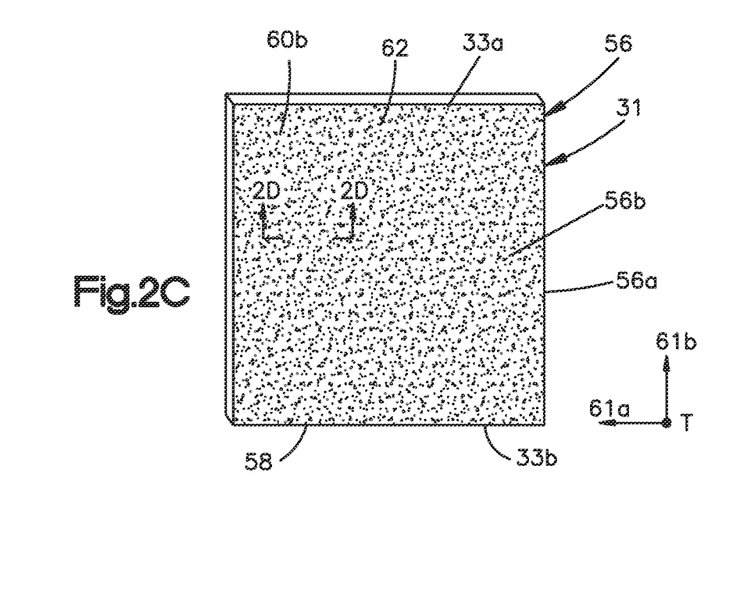
FIG. 2C is a perspective view of a second substrate.
Figure 2D:
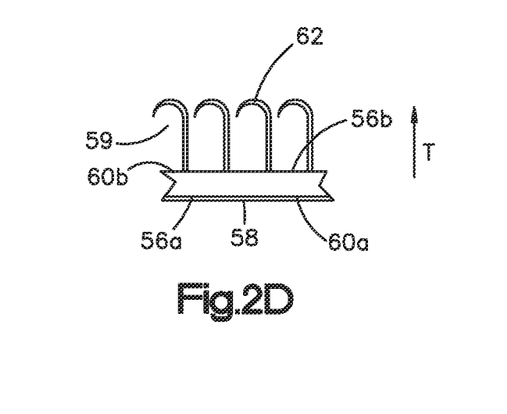
FIG. 2D is a sectional side elevation view of a portion of the second substrate illustrated in FIG. 2C, taken along line 2D-2D.

Referring now also to FIGS. 2C-2D, it should be appreciated that the auricular support system 20 can include as many substrates as desired. For instance, the at least one substrate 27 illustrated in FIG. 1A can include the substrate 28 illustrated in FIG. 2A, which can be provided as a first substrate, as well as a second substrate 31 that can be constructed in any manner as described above with respect to the substrate 28. Thus, it should be appreciated that the second substrate 31 can be constructed substantially identically or differently with respect to the substrate 28. For instance, as described above, the first end 56a can extend substantially in at least a first direction 61a. The first end 56a can further extend substantially in at least a second direction 61b that is angularly offset, such as perpendicular, with respect to the first direction 61a. It should be understood that at least one or both of the first direction 61a and the second direction 61b can be substantially linear, curved, or undulating before or after application to the dermal surface 26. The transverse direction T can extend substantially perpendicular to one or both of the first or second directions 61a-b.

The second substrate 31 can be dimensioned differently, such as smaller or greater, than or the same as the substrate 28 in one or both of the first or second directions 61a-b. The second substrate 31 can further be shaped differently than or the same as the substrate 28. In accordance with the illustrated embodiment, the second substrate 31 is larger than the substrate 28 along both the first and second directions 61a-b, and is sized to be attached to the dermal surface 26 at a location posterior of the outer ear, for instance at a location medially with respect to the helical rim 32. The substrate 28 is sized to be attached to the dermal surface 26 at a location cranially with respect to the outer ear, for instance at a location medially with respect to the helical rim 32. It should be appreciated, of course, that either substrate 28 or 31, or any additional substrate included in the auricular support system 20, can be positioned anywhere as desired such that the mold material is configured to attach to both the auricular structure 22 and the substrates in the manner described above.

Figures 3A, 3B, 3D:
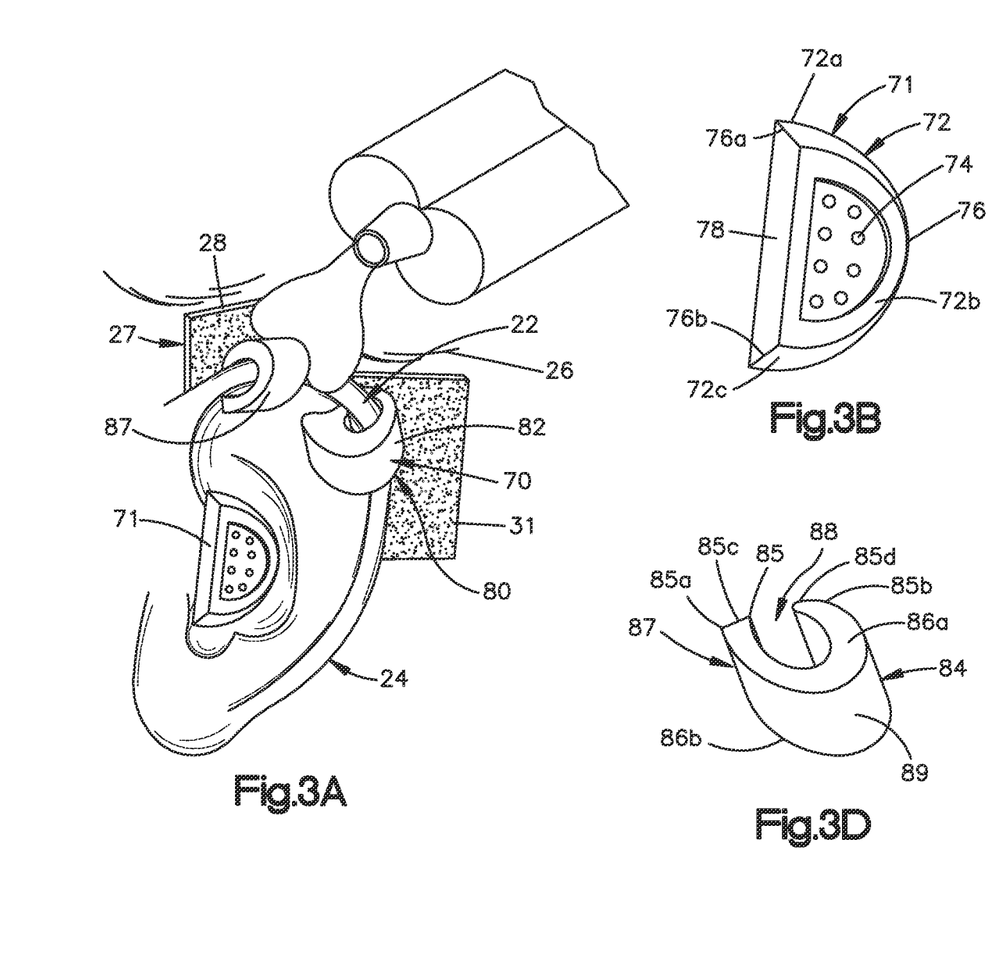
FIG. 3A is a schematic perspective view of the auricular support system illustrated in FIG. 1A, further including auxiliary ear support structure.
FIG. 3B is a perspective view of one of the auxiliary ear support structure illustrated in FIG. 3A, shown configured as a conchal cavity former.
FIG. 3D is a perspective view of one of the auxiliary ear support structure illustrated in FIG. 3A, shown configured as a retractor sized differently with respect to the retractor illustrated in FIG. 3C.

Referring now to FIG. 3A, the auricular support system 20 can further include at least one auxiliary support structure 70 that is configured to attach to a respective auricular structure. Thus, it should be appreciated that the mold material 30 is configured to attach to a first auricular structure 22, and the auxiliary support structure 70 is configured to attach to a second auricular structure, which can be the same as, included in, or different than, the first auricular support structure 22. The mold material 30 is further configured to be applied to the auxiliary support structure 70 so as to support the at least one auxiliary support structure 70 relative to the substrate 28. For instance, the mold material 30 is configured to mold about at least a portion up to all of the auxiliary support structure 70 and subsequently cure to the auxiliary support structure 70 along with the auricular structure 22, and further attach to the at least one substrate 27 as described above.

Referring now to FIGS. 3A-B, the at least one auxiliary support structure 70 can include a conchal cavity former 71 that is sized and configured to be inserted into the conchal cavity 48 (see FIG. 1A). Thus, the conchal cavity former 71 includes a conchal cavity former body 72 that can include a first auricle-facing surface 72a that is configured to face the auricle 24 when attached to the auricle 24, and second surface 72b opposite the first surface 72a. The conchal cavity former 71 can further include one or more apertures 74 extending from the second surface 72b toward the first surface 72a. For instance, the apertures 74 can extend from the second surface 72b through the first surface 72a. The apertures 74 are configured to receive the mold material 30, such that the mold material 30 can flow from the second surface 72b toward, for instance to, the first surface 72a so as to strengthen the attachment of the mold material 30 to the conchal cavity former 71 when the mold material 30 cures.

The conchal cavity former body 72 can define at least one side surface 72c that extends between the first and second surfaces 72a-b. For instance, the at least one side surface 72c can include a first curved portion 76 that defines first and second opposed terminal ends 76a-b, and a second substantially linear portion 78 that extends substantially linearly between the first and second terminal ends 76a-b. It should be appreciated that the second substantially linear portion 78 can have a curvature (including a zero curvature) that is less than the curvature of the first curved portion 76. The at least one side surface 72c is thus contoured to conform to a healthy conchal cavity. It should be appreciated that the auricular support system 20 can include a plurality of conchal cavity formers 72 having different sizes and shapes suitable to correspond to differently sized conchal cavities of different infants.

Thus, when the conchal cavity 48 (see FIG. 1A) has an anatomical abnormality, the conchal cavity former 71 having a desired size and shape that is different than the abnormal size and shape can be inserted into the abnormal conchal cavity 48, thereby causing the conchal cavity 48 to generally conform to the size and shape of the conchal cavity former 71. The attachment of the mold material 30 to the conchal cavity former 71, the auricular structure 22, and the at least one substrate 27 retains the conchal cavity former 71 with respect to the at least one substrate 27, and thus also to the dermal surface 26. In this regard, reference to attachment of the mold material to the dermal surface 26 can further include attachment to the at least one substrate 27 that is, in turn, attached to the dermal surface 26. When the mold material 30 is removed from the auricular structure 22 and the dermal surface 26, the attachment of the mold material 30 to the conchal cavity former 71 can cause the mold material 30 to remove the conchal cavity former 71 from the conchal cavity 48. Alternatively, the mold material 30 can be removed from the conchal cavity former 71, and the conchal cavity former 71 can then be removed from the conchal cavity 48.

Figure 3C:
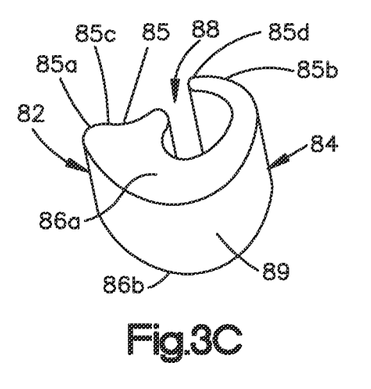
FIG. 3C is a perspective view of one of the auxiliary ear support structure illustrated in FIG. 3A, shown configured as a retractor.

Referring to FIG. 3A and FIGS. 3C-3D, the at least one auxiliary support structure 70 can include at least one splint 80, alone or in combination with the conchal cavity former 71. For instance, the at least one splint 80 can include a plurality of splints 80, including a first splint 82 and a second splint 87 that are each configured to attach to respective auricular structure, which can be the same as, included in, or different than the auricular structure 22 to which the mold material 30 is applied. For instance, as illustrated in FIG. 3C, the first splint 82 can include a splint body 84 that defines a first anatomical-facing surface 85 and a second surface 89 that is opposite the first surface 85. For instance, the first surface 85 can define first and second opposed terminal ends 85a and 85b, and the second surface 89 can extend from the first terminal end 85a to the second terminal end 85b. The second surface 89 can be convex and curved along its extension between the first terminal end 85a and the second terminal end 85b, for instance from the first terminal end 85a to the second terminal end 85b. Thus, the second surface 89 can have a curvature that is greater than the curvature of the first surface 85 (which can have a curvature of zero). The splint body 84 can further define opposed end surfaces 86a and 86b, respectively, that each can extend between the first and second surfaces 85 and 89. The end surfaces 86a and 86b can be substantially planar or alternatively shaped as desired.

The splint 82 can define a gap 88 that extends at least into the splint body 84. For instance, the gap 88 can extend from the first end surface 86a to the second end surface 86b, and can further extend into the first surface 85 along a direction toward the second surface 89, and can terminate in the splint body 84 without extending through to the second surface 89, or can alter. Thus, the first surface 85 can define a first region 85*c* and a second region 85*d*, such that the gap 88 is disposed between the first and second regions 85*c* and 85*d*. The gap 88 can be sized to receive an auricular structure. For instance, the gap 88 can be sized to receive the helical rim 32 or auricular lobe such that the first region 85*c* of the first surface 85 is configured to face or abut the auricle, for instance at the antihelix 36. Thus, the first region 85*c* can be substantially planar, curved, or undulating so as to define a desired anatomical geometry of the antihelix 36. Further, the gap 88 can be sized and shaped so as to define desired anatomical geometry of the helical rim 32. In this regard, it should be appreciated that the helical rim 32 can define a second auricular structure to which the at least one auxiliary support structure 70 is configured to be attached. It should be appreciated that the auricular support system 20 can include a plurality of the splints 82, having different sizes and shapes so as to correspond to the helical rims of different infants. For instance, the gaps 88 can be of different sizes and curvatures, and depths, different distances between the end surfaces 86*a* and 86*b*, and different geometries of the first region 85*c* of the first surface 85.

Thus, when at least one or both of the helical rim 32 and the antihelix 36 has an anatomical abnormality, the splint 82 having an appropriate size can receive the helical rim 32 and abut or face the antihelix 36, thereby causing the helical rim 32 generally conform to the size and shape of the gap 88, and further causing the antihelix to generally conform to the surface geometry of the first region 85*c*, for instance if the first region 85*c* abuts the antihelix 36. Thus, the splint 82 can further maintain the helical rim 32 at a desired spatial relationship with respect to the antihelix. Further, the splint 82 can be disposed relative to the dermal surface 26 at a desired spacing so as to correct the anatomical spacing between the helical rim 32 and the dermal surface 26. In this regard, the splint 82 can be referred to as a retractor, as the splint 82 can maintain the helical rim 32 in a retracted state, thereby decreasing the distance between the helical rim 32 and the dermal surface 26. The introduction of the mold material 30 to the auricular structure 22, the splint 82, and the dermal surface 26 including the at least one substrate 27, and subsequent curing of the mold material 30 about the auricular structure 22, the splint 82, and the dermal surface 26 including the at least one substrate 27, can thus retain one or both of the helical rim 32 and the antihelix 36 in an anatomically corrected position. When the mold material 30 is removed from the auricular structure 22 and the dermal surface 26, the attachment of the mold material 30 to the splint 82 can cause the mold material 30 to remove the splint from the auricle. The mold material 30 can be removed from the dermal surface 26 by removing the respective at least one substrate 27 from the dermal surface 26. Alternatively, the mold material 30 can be removed from the respective at least one substrate 27 while the at least one substrate 27 is attached to the dermal surface. The mold material 30 can alternatively be removed from the splint 82, and the splint 82 can then be removed from the helical rim 32. While the gap 88 has been described as sized to receive the helical rim 32, it should be appreciated that the gap 88 can alternatively receive the lobule 46, so as to correct for a lobular defect as desired.

Referring now to FIGS. 3A and 3D, the second splint 87 can be constructed as described above with respect to the first splint 82, with the exception that the splint body 84 can be sized and shaped differently than the splint body 84 of the first splint 82. For instance, at least one or more up to all of the first and second surfaces 85 and 87, including the first region 85*c* of the first surface 85, of the second splint 87 can be sized and shaped differently than those of the first splint 82. Furthermore, the gap 88 of the second splint 87 can be sized and shaped differently than the gap 88 of the first splint 82. In accordance with the illustrated embodiment, the gap 88 of the second splint 87 can be sized to receive the helical rim 32 at the cranial end of the auricle, and the first region 85*c* of the first surface of the second splint 87 can be configured to face or abut one or both of the triangular fossa 34 and the helical crux 35 (see FIG. 1A).

The attachment of the mold material 30 to the auricular structure 22, the second splint 87, and the dermal surface 26 can thus retain one or more up to all of the helical rim 32, the triangular fossa 34, or the helical crux 35 in an anatomically corrected position. When the mold material 30 is removed from the auricular structure 22 and the dermal surface 26, the attachment of the mold material 30 to the splint 87 can cause the mold material 30 to remove the splint 87 from the auricle. Alternatively, the mold material 30 can be removed from the splint 87, and the splint 87 can then be removed from the helical rim 32. While the gap 88 of the second splint 87 has been described as sized to receive the helical rim 32, it should be appreciated that the gap 88 can alternatively receive the lobule 46, so as to correct for a lobular defect as desired.

Figure 3E:
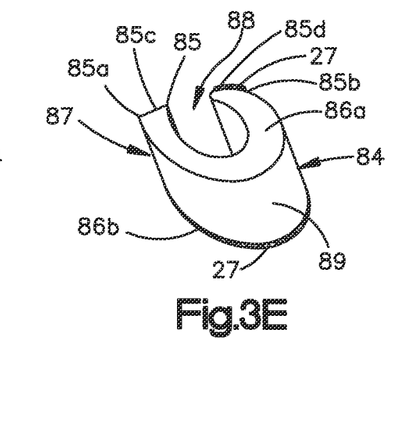
FIG. 3E is a perspective view of the ear support structure illustrated in FIG. 3D, shown attached to a substrate.

Any of the splints 80, for instance the second splint 87 as illustrated in FIG. 3E, can include one or more sections of the at least one substrate 27 that is attached to an outer surface of the splint 87. For instance, as described above, the splint 87 can include the first region 85*c* that is configured to face or abut one or both of the triangular fossa 34 or the helical crux 35, The second region 85*d* is positioned such that when the splint 80 is mounted onto the auricle 24 so that the helical rim 32 is received in the gap 88, the second region 85*d* can face the dermal surface 26, and thus the substrate 28.

Accordingly, at least one or more portions of the at least one substrate 27 can be attached to the outer surface of the second region 85*d*. In particular, the adhesive 58, and thus the first end 56*a*, can be attached to the second region 85*d*, such that the second end 56*b*, and thus the fingers 62, face the substrate 28. The fingers 62 of the substrate 28 that is attached to the dermal surface 26 can define one of hooks and loops, and the fingers 62 of the at least one substrate 27 that is attached to the splint 80 can define the other of hooks and loops. Accordingly, the fingers 62 of the at least one substrate 27 that is attached to the splint 80, and in particular to the second region 85*d*, can attach to the substrate 28 that is attached to the dermal surface 26. Thus, the second region 85*d* can define a thickness sufficient such that a desired spacing is maintained between the auricle 24 and the dermal surface 26 when the at least one substrate 27 of the second region 85*d* is attached to the substrate 28.

Further, when the splint 80 is mounted onto the auricle 24 so that the helical rim 32 is received in the gap 88, the second end surface 86*b* can face the second substrate 31. Accordingly, at least one or more portions of the at least one substrate 27 can be attached to the second end surface 86*b*. In particular, the adhesive 58, and thus the first end 56*a*, can be attached to the second end surface 86*b*, such that the second end 56*b*, and thus the fingers 62, face the second substrate 31. The fingers 62 of the second substrate 31 that is attached to the dermal surface 26 can define one of hooks and loops, and the fingers 62 of the at least one substrate 27 that is attached to the splint 80 can define the other of hooks and loops. Accordingly, the fingers 62 of the at least one substrate 27 that is attached to the splint 80, and in particular to the second end surface 86b, can attach to the second substrate 31 that is attached to the dermal surface 26. Thus, the splint 80 can define a length from the first end surface 86a to the second end surface 86b that is sufficient such that a desired spacing is maintained between the auricle 24 and the dermal surface 26 when the at least one substrate 27 of the second end surface 86b is attached to the second substrate 31. While the at least one substrate 27 that is attached to the second end surface 86b can be attached to the second substrate 31 as described above, it should be appreciated that the at least one substrate 27 that is attached to the second end surface 86b can alternatively be attached to a second region 33b of the at least one substrate 56 illustrated in FIG. 4A and described in more detail below.

It should be appreciated that the auricular support system 20 can include a plurality of splints, including a plurality the first splints 82, a plurality of the second splints 87, and a plurality of any suitable alternatively constructed splint that is configured to attach to an auricular structure so as to correct an auricular deformity in the auricular structure to which it is attached.

Figure 4A:
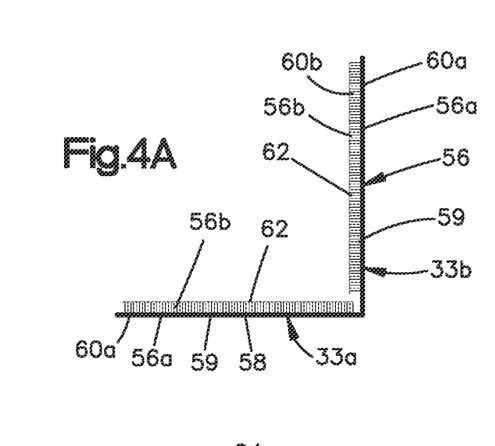
FIG. 4A is a sectional side elevation view of a substrate similar to the substrate illustrated in FIGS. 2B-C, but constructed in accordance with an alternative embodiment.
Figure 4B:
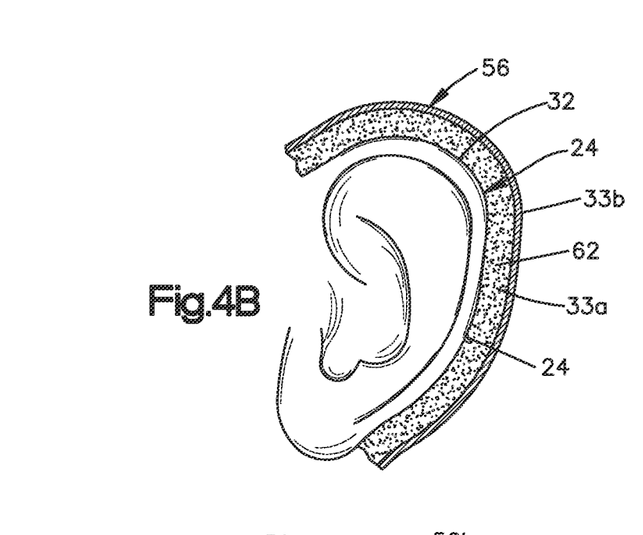
FIG. 4B is a front elevation view of the substrate illustrated FIG. 4A, but shown attached to a dermal surface adjacent an auricle.
Figure 4C:
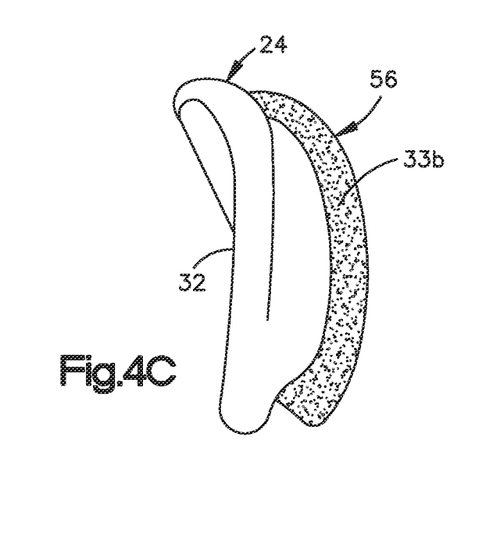
FIG. 4C is a perspective view of the substrate illustrated FIG. 4A, shown attached to the dermal surface adjacent an auricle illustrated in FIG. 4B.

Referring now to FIGS. 4A-4C, it should be appreciated that one or more up to all of the substrates 27 can be constructed in accordance with any suitable alternative embodiment. The one or more of the substrates 27, alone or in combination, can substantially surround a portion up to substantially all of the auricle 24. For instance, the at least one substrate 27 can include a single substrate that substantially surrounds the helical rim 32 as illustrated in FIG. 4B. Alternatively, as illustrated in FIGS. 1A and 3A, the at least one substrate 27 can include a plurality of substrates that in combination substantially surround at least a portion up to all of the helical rim 32.

As illustrated in FIGS. 4A-4C, the substrate body 56 can define a first region 33a and a second region 33b that can be substantially coplanar with the first region 33a as illustrated in FIGS. 2B-C. Alternatively, the second region 33b can be orientated angularly offset, such as substantially perpendicular, with respect to the first region 33a. Thus, the first region 33a can be configured to attach to the dermal surface 26, such that the second region 33b, including the first and second surfaces 60a and 60b of the second region 33b, extends out from the dermal surface 26 at a non-zero angle with respect to the dermal surface 26. For instance, the second region 33b, including the first and second surfaces 60a and 60b of the second region 33b, can extend substantially perpendicular with respect to the dermal surface 26. The first end 56a, such as the first surface 60a, of the first region 33a can thus carry the adhesive 58. For instance, the first end 56a, such as the first surface 60a, of the second region 33b can be devoid of exposed adhesive 58. In accordance with one embodiment, the first end 56a, such as the first surface 60a, of the second region 33b can be devoid of the adhesive 58. In accordance with another embodiment, the first end 56a, such as the first surface 60a, of the second region 33b can carry the adhesive 58 that is covered by a backing, such that the adhesive 58 is not exposed. In this regard, it should be appreciated that the first end 56a, such as the first surface 60a, of the first region 33a can carry the adhesive 58 that is covered by a backing that is removable so as to expose the adhesive 58. In the embodiments illustrated in FIGS. 2B-C, the first end 56a, such as the first surface 60a, of the first and second regions 33a and 33b can carry the adhesive by a backing that is removable so as to expose the adhesive 58.

In the embodiments illustrated in FIGS. 2B-C and 4A-C, the at least one void 59 such as a plurality of voids that are configured to receive the mold material 30 can be defined by the second end 56b of the second region 33b alone or in combination with the first region 33a. Thus, the second region 33b, alone or in combination with the first region, can define the matrix that defines the plurality of voids 59. It should be appreciated that the first end 56a of the second region 33b alone or in combination with the first region 33a can define the first surface 60a and the opposed second surface 60b that is spaced from the first surface along 60a along the transverse direction T. The first surface 60a of one or both of the first or second regions 33a and 33b can carry the adhesive 58 in the manner described above. The second region 33b, alone or in addition to the first region 33a, can include the fingers 62 that project from the second surface 60b in the manner described above. Thus, the substrate body 56, for instance at the second end 56b of the second region 33b, alone or in combination with the first region 33a, can define a matrix of fingers 62 that project out from the second surface 60b so as to define the voids 59. Accordingly, during operation, when the mold material 30 is received in the voids 59, such that the fingers 62 are embedded in the mold material 30, the mold material 30 can cure so as to attach the mold material to the second region 33b alone or in combination with the first region 30a in the manner described above. It should be appreciated that the second substrate 31, along with any additional substrates of the auricular support system 20, can include the first and second regions 33a and 33b in accordance with any embodiment as described herein.

Figure 4D:
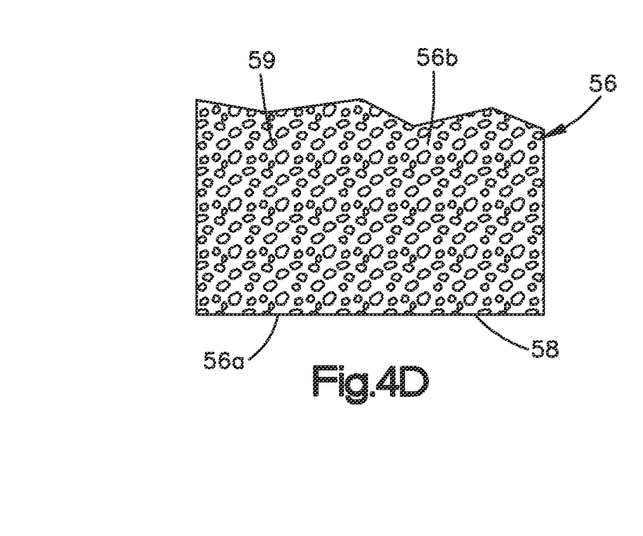
FIG. 4D is a perspective view of a substrate constructed in accordance with another alternative embodiment.

Referring to FIG. 4D, it should be appreciated that the first and second substrates 28 and 31, or any other substrate of the auricular support system 20 can be constructed in accordance with any suitable alternative embodiment so as to be attachable to the dermal surface 26 and define at least one void 59 such as a plurality of voids 59 that are suitable to receive the mold material 30, such that the mold material 30 is attached to the substrate when the mold material 30 is cured. For instance, in accordance with one embodiment, the body of the at least one substrate 27 can define a sponge matrix that defines the voids 59. The voids 59 can be elongate along a direction that includes the transverse direction T substantially alone or in combination with a direction that is perpendicular to the transverse direction, such that the voids that the voids can be disposed between the first end 56a and a portion of the second end 56b, which can be defined by the sponge matrix, along the transverse direction T. The first end 56a can be coated with or otherwise include the adhesive 58 that is configured to attach to the dermal surface 26 in the manner described above.

It should be appreciated that a kit can be provided that can include at least one or more, such as a plurality, of at least one or more up to all of the mold material 30, the at least one substrate 27, and the at least one auxiliary support structure 70. At least one of the at least one substrate 27 of the kit can be constructed having a different size and shape with respect to another one of the at least one substrate 27 of the kit in the manner described above. Further, at least one of the auxiliary support structure 70 can be constructed having a different size and shape with respect to another one of the support structure 70 of the kit in the manner described above.

A method for improving an auricular deformity can thus include the steps of attaching at least a portion of a first end of a substrate to a dermal surface, the substrate including a second end that defines at least one void, applying a mold material to both an articular structure and at least a portion of the substrate such that at least a portion of the mold material is embedded in the void, and after the applying step, allowing the mold material to cure so as to support the auricular structure relative to the substrate. The attaching can further include the step of attaching at least a portion of a first surface of the first end of the substrate to the dermal surface. The applying step can further include the step of applying the mold material to at least one finger of the substrate that extends from out a second surface of the first end that is opposite the first surface, so as to embed the at least one finger in the mold material. The substrate can include a plurality of fingers that project from the second surface, and the applying step can further include the step of embedding the plurality of fingers in the mold material. The attaching step can further include the step of attaching the first surface of a first region of the substrate to the dermal surface, such that a second region of the substrate projects out from the dermal surface at a non-zero angle with respect to the first region. The attaching step can further include the step of orienting the second region substantially perpendicular to the first region. The plurality of fingers can extend out from the second surface at the first region, and the applying step can further include coating at least a portion of the second surface with the mold material at the first region so as to embed the plurality of fingers in the mold material. The plurality of fingers can further project out from the second surface at the second region, and the applying step can further include coating at least a portion of the second surface with the mold material at the second region so as to embed the plurality of fingers in the mold material.

The auricular structure can be a first auricular structure, and the method can further include the step of attaching at least one auxiliary support structure to a second auricular structure. The applying step can further include the step of applying the mold material to the auxiliary support structure so as to support the at least one auxiliary support structure relative to the substrate. The at least one auxiliary structure comprises a splint including a splint body that defines a gap, and the method further comprises the step of receiving the second auricular structure in the gap. The splint can be a helical rim retractor and the second auricular structure includes a helical rim, and the receiving step can include the step of receiving a helical rim in the gap. The at least one auxiliary support structure can include a conchal cavity former, the second auricular structure can include a conchal cavity, and the method can further include the step of inserting the conchal cavity former into a conchal cavity.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments described herein. Furthermore, it should be appreciated that apparatus and methods described in connection with one embodiment can be equally applicable to all other embodiments unless otherwise indicated. One of ordinary skill in the art will readily appreciate from the present disclosure that apparatus and methods presently existing or later to be developed that perform substantially the same function or achieve substantially the same result as the corresponding embodiments described herein may be utilized according to the present invention. Thus, it will be appreciated by those skilled in the art that various modifications and alterations of the invention can be made without departing from the broad scope of the appended claims. Some of these have been discussed above and others will be apparent to those skilled in the art.

What is claimed is:

1. An auricular support system for correcting an auricular deformity on an outer ear of a human subject, the auricular support system comprising:
a first substrate configured to attach to a dermal surface around the posterior side of the outer ear of the human subject;
a second substrate configured to project transversely from the dermal surface and first substrate, the second substrate comprising a curved shape for curving around a helix of the outer ear;
at least one splint configured to attach to the outer ear, to the first substrate, and to the second substrate, the at least one splint configured to hold the outer ear in a desired configuration; and
means for maintaining a position of the at least one splint and the desired configuration of the outer ear relative to the dermal surface.

2. The auricular support system of claim 1, wherein the at least one splint comprises a plurality of splints configured to attach to the outer ear.

3. The auricular support system of claim 1, further comprising a container having a dispenser defining an outlet opening.

4. The auricular support system of claim 1, wherein the means for maintaining the position of the at least one splint and the desired configuration of the outer ear relative to the dermal surface comprises a first attachment element on each of the first substrate and second substrate and a second attachment element on the at least one splint configured to mate with the first attachment element on each of the first substrate and second substrate to interconnect the first substrate, the second substrate and the at least one splint.

5. The auricular support system of claim 1, wherein the second substrate projects perpendicularly relative to the first substrate.

6. The auricular support system of claim 1, wherein the first substrate comprises a first side having an adhesive for attaching the first substrate to the dermal surface.

7. The auricular support system of claim 6, wherein the first substrate comprises a second side opposite the first side, the second side comprising a first material, the first material comprising one of a hook material and a loop material that forms part of the means for maintaining the position of the at least one splint and the desired configuration of the outer ear relative to the dermal surface.

8. The auricular support system of claim 7, wherein the second substrate comprises a second material, the second material identical to the first material and forming part of the means for maintaining the position of the at least one splint and the desired configuration of the outer ear relative to the dermal surface.

9. The auricular support system of claim 8, wherein the at least one splint comprises a third material, the third material being another of one of said hook material and said loop material configured for mating with the first material and with the second material to attach the at least one splint to the first substrate and the second substrate, the third material forming part of the means for maintaining the position of the at least one splint and the desired configuration of the outer ear relative to the dermal surface.

10. The auricular support system according to claim 1, wherein the first substrate and the second substrate are separate pieces configured to be independently manipulated from one another.

11. The auricular support system according to claim 1, wherein the first substrate and the second substrate are dimensioned differently.

12. An auricular support system for correcting an auricular deformity on an outer ear of a human subject, the auricular support system comprising:
- a first substrate;
- a second substrate projecting transversely from the first substrate, the second substrate comprising a curved shape;
- at least one splint attached directly to the first substrate and directly to the second substrate, the at least one splint configured to hold the outer ear in a desired configuration; and
- means for maintaining a position of the at least one splint and the desired configuration of the outer ear relative to a dermal surface.

13. An auricular support system for correcting an auricular deformity on an outer ear of a human subject, the auricular support system comprising:
- a first substrate configured to attach to a dermal surface adjacent to the outer ear;
- a second substrate configured to be attached to and project transversely from the first substrate, the second substrate comprising a curved shape for curving around a portion of the outer ear;
- at least one splint configured to attach to and apply force to the outer ear, the at least one splint configured to hold the outer ear in a desired configuration; and
- means for maintaining a position of the at least one splint and the desired configuration of the outer ear relative to the dermal surface.

14. An auricular support system according to claim 13, wherein said curved shape terminates at opposite ends of said second substrate without said second substrate completely surrounding the outer ear.

15. An auricular support system according to claim 13, wherein the first substrate is configured to attach adjacent to the outer ear without the first substrate completely surrounding the outer ear.

16. An auricular support system according to claim 13, wherein the at least one splint is configured to touch the second substrate.

* * * * *